United States Patent
Care et al.

(10) Patent No.: US 7,486,071 B2
(45) Date of Patent: Feb. 3, 2009

(54) FLUID MONITORING ARRANGEMENT

(75) Inventors: Ian C D Care, Derby (GB); Timothy A Shepherd, Derby (GB)

(73) Assignee: Rolls-Royce plc, London (GB)

( * ) Notice: Subject to any disclaimer, the term of this patent is extended or adjusted under 35 U.S.C. 154(b) by 907 days.

(21) Appl. No.: 10/884,990

(22) Filed: Jul. 7, 2004

(65) Prior Publication Data

US 2005/0024053 A1 Feb. 3, 2005

(30) Foreign Application Priority Data

Jul. 29, 2003 (GB) .................. 0317675.7

(51) Int. Cl.
G01V 3/00 (2006.01)
(52) U.S. Cl. .................. 324/306; 324/303
(58) Field of Classification Search ......... 324/300–322; 600/407–455; 250/287; 73/151
See application file for complete search history.

(56) References Cited

U.S. PATENT DOCUMENTS

| | | | | |
|---|---|---|---|---|
| 4,785,245 A * | 11/1988 | Lew et al. | .................. | 324/308 |
| 4,926,120 A | 5/1990 | Veronesi | | |
| 5,072,732 A * | 12/1991 | Rapoport et al. | ............ | 600/415 |
| 5,169,785 A | 12/1992 | Altman | | |
| 5,371,464 A * | 12/1994 | Rapoport | .................... | 324/306 |
| 5,532,593 A * | 7/1996 | Maneval et al. | ............ | 324/306 |
| 6,194,900 B1 * | 2/2001 | Freeman et al. | ............ | 324/321 |
| 6,346,813 B1 * | 2/2002 | Kleinberg | .................. | 324/303 |

(Continued)

FOREIGN PATENT DOCUMENTS

EP    0 451 962 A    10/1991

(Continued)

OTHER PUBLICATIONS

Powrie, H., "Use of Electrostatic Technology for Aero Engine Oil System Monitoring", 2000 IEEE Aerospace Conference, Mar. 18, 2000, entire document.

(Continued)

*Primary Examiner*—Brij B Shrivastav
(74) *Attorney, Agent, or Firm*—W. Warren Taltavull; Manelli Denison & Selter PLLC

(57) ABSTRACT

A fluid monitoring arrangement 1 for an engine is operated in accordance with a method whereby nuclear magnetic resonance (NMR) interrogation of the fluid flow 3 it is possible to determine whether appropriate fluids and additives are being utilised as well as whether potential detrimental actions occur such as engine wear and carbonisation through particulate components within the flow 3. Generally, an expected signal response from the fluid flow 3 is determined and the actual signal response compared in a comparator 8 with that expected signal response. Divergence in the actual signal response and in particular with regard to its profile is identified and an indication provided in a display 10 with regard to the potential coolant of such divergence. Normally, a reference library 11 is provided of expected signal responses for comparison in the comparator with the actual signal responses. The library 11 stores reference responses for known causes of deviation in the signal response from the NMR interrogation. Thus, by a best fit comparison a prediction as to the cause of divergence as a result of erroneous use of fluids or additives within the fluid flow 3 can be highlighted.

26 Claims, 1 Drawing Sheet

Figure 1:
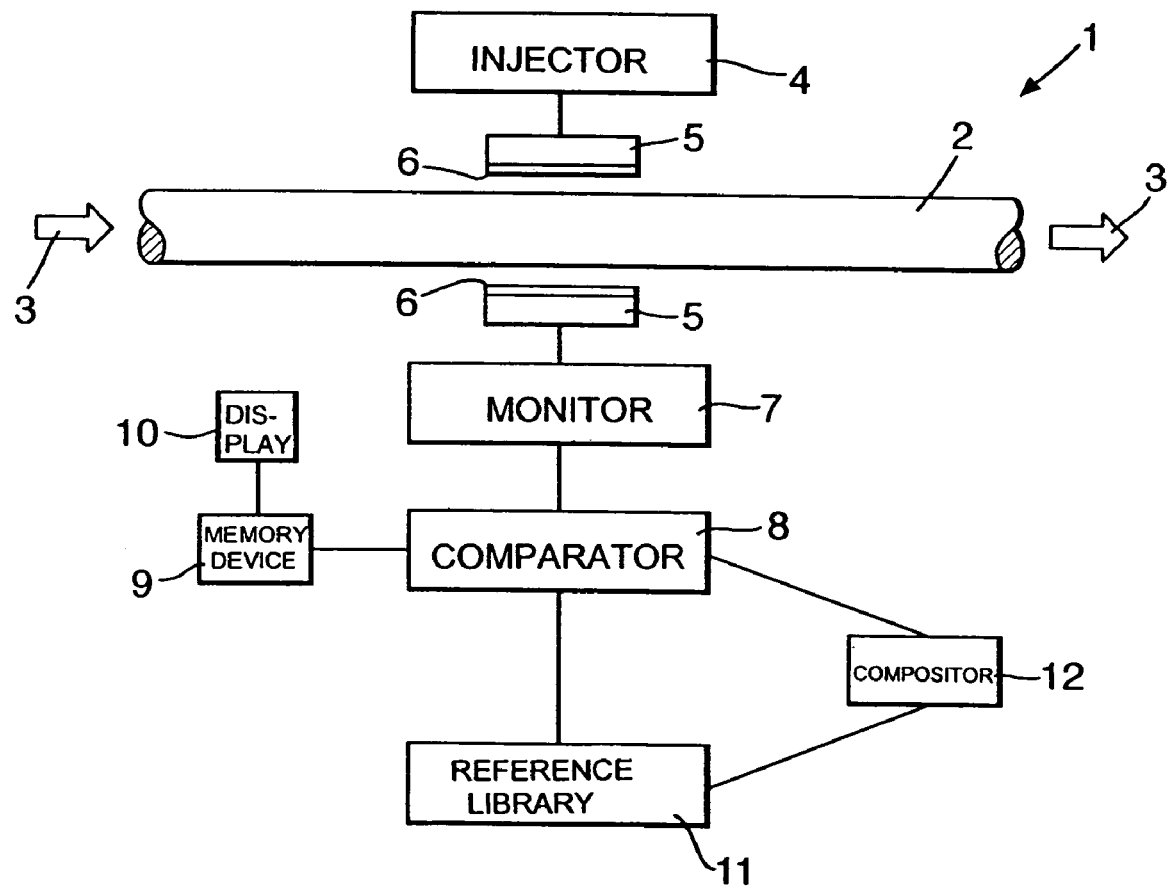

U.S. PATENT DOCUMENTS 6,794,865 B2 * 9/2004 Astley et al. ................ 324/306
7,164,123 B2 * 1/2007 Morris et al. ............... 250/287

FOREIGN PATENT DOCUMENTS

EP   1 191 330   3/2002
EP   1 191 330 A   3/2002

OTHER PUBLICATIONS

Miller, J., "In-Line Oil Debris Monitor for Aircraft Engine Condition Assessment", 2000 IEEE Aerospace Conference, Mar. 18, 2000, entire document.

* cited by examiner

FLUID MONITORING ARRANGEMENT

FIELD OF THE INVENTION

The present invention relates to fluid monitoring arrangements and more particularly to such arrangements used with fluid monitoring in engines, with particular regard to service critical turbine engines used for example in aircraft.

BACKGROUND OF THE INVENTION

Engines, and in particular turbine engines, include a number of fluids which are consumable in that they deteriorate with time and operational conditions. It is also true that various components within an engine wear and debris from that wearing process become entrained within the fluids. A number of techniques have been devised for elucidating the condition of lubricants, coolants and other consumables within an engine along with determination of particulate debris within fluid flow circulated within an engine. One example of such an approach is using nuclear magnetic resonance (NMR) and one method is outlined in U.K. patent application no. 0022587. In short, NMR signals are presented to the fluidic flow such that variations in the fluid as well as debris content are detected by response signal frequency shift and broadening. These frequency shifts and response signal provide indications of the fluidic flow condition in terms of constituent component fluids as well as deterioration in those components through combustion and particulate content reflective of wear debris. This technique is non intrusive in that the fluid flow can be analysed in situ by locating appropriate sensors around a conduit for that fluid flow. Nevertheless, analysis generally takes several minutes and so is difficult to utilise with respect to closed loop control of engine function.

Some engine purchase or management schemes closely tie payment to the period of time for which the engine is powered up with charging on a unitary basis. In such circumstances if the engine is not properly operated such calculations with regard to costs of operating of the engine are significantly prejudiced. In short, if incorrect consumable fluids are used the engine will not be operating in accordance with manufacturer's specifications and so the engine will require earlier and probably remedial servicing. Such servicing costs and remedial action will fall upon the leaser of the engine rather than the operator who clearly has an incentive to use inferior and therefore probably cheaper consumable fluids etc. In such circumstances a means for verifying appropriate operation of the engine is required.

SUMMARY OF THE INVENTION

In accordance with the present invention there is provided a monitoring arrangement for a fluid flow in a conduit, the arrangement comprising an NMR interrogation monitor associated with the conduit for fluid flow, the NMR interrogation monitor interrogating that fluid flow by actual response signal classification by a comparator for comparison of said fluid flow with an expected response signal and the monitor providing a specific indication as to divergence of that actual response signal from the expected response signal dependent upon the cause of that divergence.

Also in accordance with the present invention there is provided a method of engine monitoring a fluid flow in conduit, the method comprising monitoring the fluid flow utilising NMR interrogation to provide an actual signal, establishing an expected response signal for that NMR interrogation, comparing the actual response signal with the expected response signal and providing a specific indication as to divergence of that actual response signal from the expected response signal dependent upon the cause of that divergence.

Typically, NMR interrogation is to deduce fluid flow constituents and/or particulate content within that fluid flow.

Generally, NMR interrogation determines specific fluid flow component nuclei and/or frequency shift/line broadening of the actual response signal compared to the expected response signal.

The fluid flow is preferably in a conduit of a turbine engine.

Normally, the comparison between the actual response signal and the expected response signal allows determination of one or more of the following:—
  a) Difference of base carrier fluid in the fluid flow from that expected or required;
  b) Presence or absence of relative quantity of a specific additive expected within the fluid flow;
  c) Determination of debris due to engine wear or other degradation entrained within the fluid flow;
  d) Determination of carbonisation and/or combustion particulates in the fluid flow;
  e) Determination of nature of any external contaminants present in the fluid flow (gas/liquid/solid).

Possibly, where there is a difference of the base carrier fluid, the indication is to the actual carrier fluid within the fluid flow.

Possibly, where determination is relative to a specific additive then the indication provides a list as to the missing additive and/or its quantity if different from that expected or required.

Possibly, where determination is of debris due to engine wear or other degradation then the indication identifies the particular engine component and/or region of the engine worn or degraded.

Possibly, where the determination is of carbonisation or combustion particulates in the fluid flow then the indication is indicative of excess fluid flow temperature and/or possible identification as to the part of the engine subject to that excessive temperature.

Possibly, where the determination is of external contamination then the indication is indicative of unauthorised material put into the fluid system.

Normally, the comparator operates by an equivalent comparison criteria between the actual signal and the expected signal determined upon acceptable similarity margins. Possibly, that similarity margin is variable dependent upon actual engine monitoring requirements.

Generally, when that equivalent comparison criteria is not met then the actual response signal is analysed for cause of divergence by comparison with a look up table of known response signals. Possibly, that look up table comprises a number of response signals for predictable causes of divergence and the comparison forms a best fit comparison to provide an indication as to the probable cause of divergence. Possibly, a ranked list of causes of divergence is provided. Alternatively, the look up table comprises known response signals for reference fluid constituents and/or additives and/or possible debris and/or combustion particulates and a compositor projects those known response signals upon the actual signal response for a predictive cause of divergence as an indication from the comparator. Possibly, such projection is by the compositor utilising iterative comparisons from a base comparison until a nearest fit to the actual signal response is found.

Generally, the indication of divergence provided by the comparator is only available upon authorised access.

Further in accordance with the present invention there is provided a turbine engine incorporating an engine monitoring arrangement as described above or that engine monitored in accordance with the method described above.

BRIEF DESCRIPTION OF THE INVENTION

An embodiment of the present invention will now be described by way of example only with reference to the accompanying drawing in which there is a schematic depiction of an engine monitoring arrangement in accordance with the present invention.

DETAILED DESSCRIPTION OF THE INVENTION

Referring to the drawing providing a schematic depiction of an engine monitoring arrangement in accordance with the present invention. It is known that engines and in particular turbine engines incorporate a number of conduits through which fluids such as lubricants, coolants and hydraulic oils flow. Thus, conduit 2 contains a fluid flow 3 in the direction of the illustrated arrow heads. Typically, in accordance with the present invention engine monitoring will be performed prior to a conduit filter (not shown) in order to allow monitoring and analysis of the fluid flow 3 constituents and components prior to removal of at least any particulates by such a conduit filter. It would be appreciated that any monitoring after such a filter would be rendered suspect or meaningless due to the removal of such particulates etc.

In accordance with the present invention a nuclear magnetic resonance (NMR) sensor arrangement 1 is provided. As indicated above, such an arrangement is described in U.K. patent application No. 0022587.0 (Rolls Royce Plc). In shorts, excitation signals are presented to the fluid flow 3 in order to achieve desired magnetic nuclear resonance. This nuclear magnetic resonance produces distinct signals for differing nuclei such that response signals provide an indication as to the constituents within that fluid flow 3.

The NMR sensor/monitor in accordance with the present invention is shown schematically in the form of an injector 4 which presents through magnetic poles 5 an excitation magnetic field for the fluid flow 3. The resonance signals are detected by coils 6. The technique and processes of NMR are relatively well known and the particular excitation frequency utilised and injected through the magnetic poles 5 is chosen dependent upon expected constituents within the fluid flow 3. Only a single sensor is shown here, multiple sensors tuned for different nuclei frequencies may be used.

The coils 6 are presented around the conduit 2 in order to become excited by the resonant nuclei within the fluid flow 3. These response signals are presented to a monitor 7 where generally there is signal filtering and other processing in order to extract from background noise and other factors actual signal responses from the fluid flow presented through the conduit 2. Generally, the actual response signals will take the form of frequency peaks within a spectrum indicative of the resonance within the atomic structure of the components within the fluid flow 3. As indicated above NMR techniques and processes are well known and documented. Similarly, techniques for signal filtering and enhanced extraction are also known and utilised dependent upon particular requirements.

Although depicted with respect to a conduit 2 in the form of a pipe it will be appreciated that fluid flow may be presented through a manifold or channel within an engine. The present engine monitoring arrangement and the method of engine monitoring associated with that arrangement can be utilised at various positions within an engine. In short, provided nuclear magnetic resonance excitation can be induced within a fluid flow and the resonant response signals detected then the present arrangement and method can be implemented at that location. However, it will be appreciated that interference, noise and other factors such as flow rate will be variable at different parts of the engine and so require greater or less signal processing for adequate response signal extraction.

The purpose of the present engine monitoring arrangement and method is to determine deviations within the fluid flow 3 from that expected or required for engine operation. These divergences from the required fluid flow 3 are determined through comparison of actual NMR response signals with expected NMR response signals for the arrangement at a particular engine location. In such circumstances, initially expected response signals are determined for fluid flow 3 through the conduit 2. The expected response signals can be determined from known fluid flow constituents but more advantageously an initial calibration of expected response signals achieves better results. Thus, upon initial engine set up, that is to say when fluids in the fluid flow 3 are known the be fresh and appropriate the response signals from the fluid flow 3 in the conduit 2 are determined through detector rings 6 and monitor 7. In such circumstances those calibration response signals are set as the expected response signals for an engine and in particular fluid flow 3 when known to be acceptable and therefore these response signals are automatically adjusted for actual engine monitoring arrangement position rather than predicted expected response signals taken from idealised reference nuclear magnetic responses for fluid flow 3 constituents. In any event, the expected response signals are stored within a comparator 8. Thus, the comparator 8 incorporates an expected response signal or signals for the fluid flow 3 when that flow incorporates the necessary base carrier fluid e.g. lubricant as well as any additives necessary for engine operation. In such circumstances, deviations from the expected response signal in the actual response signal determine through the monitor arrangement will be identified by the comparator 8.

As indicated previously generally NMR response signals take the form of frequency peaks in a predictive spectrum. The comparator 8 will therefore within accepted similarity margins compare the actual signal response with the expected signal response. If there is coincidence between the actual and the expected signal responses then no divergence indication is provided or logged. However, if there is appreciable divergence between the actual signal response and the expected signal response then a divergence indication will be flagged. As indicated above a principal utilisation of the present engine monitoring method and arrangement is with respect to illicit operation of the engine by an operator in comparison with operational procedures and rules established by the manufacturer or owner of that engine. In such circumstances, the flagged indication of divergence between the expected response signal and the actual response signal will normally indicate use of an unacceptable base carrier fluid and/or additive but will not be openly identified. Thus, the divergence indication will be stored in a memory device 9 for appropriate authorised interrogation typically at service for the engine. The memory device 9 will display upon a display 10 that there is a difference from the expected fluid flow 3 in terms of its NMR response signal. Normally the comparator 8 will also provide an indication to the memory device 9 as well as the display 10 an indication for the cause of that divergence in terms of constituent parts of the fluid flow 3.

As indicated above determination or setting of the expected signal response can be achieved through a calibration process or by predictive composition of known responses for constituent parts of the fluid flow 3. However, determination and prediction of the cause for such divergence between the actual response signal and the expected response signal will depend upon possible causes for such divergence. Thus, for example with respect to lubricant fluids it is possible to substitute the necessary high grade lubricant fluid for a lower grade lubricant fluid e.g. high performance (EP) aviation lubricant oil by base aviation lubricant oil. In such circumstances generally a reference library 11 is associated with the comparator 8 whereby once divergence beyond the similarity margin is established then the comparator 8 compares the actual signal response with the library of response signals in order to establish the cause of divergence in terms of the probable illicit use of an unacceptable base carrier fluid or lack of a particular additive either completely or below an acceptable constituent level within the fluid flow 3.

The reference library 11 can be essentially taught different response signals for particular fluid flow 3 deviations by presenting those fluid flow 3 deviations in the conduit 2 and storing in the library 11 the responses received through the detector coil 6, monitor 7 and comparator 8. In such circumstances, as described above eccentricies due to monitoring arrangement position within the engine will be accommodated within the stored reference response signals for comparison by the comparator 8. Alternatively, the reference library 11 may store reference response signals for known constituent components possible within the fluid flow 3 and then through a compositor 12 create an amalgam of such reference response signals for individual constituent components possible within the flow 3 in order to compare that predicted response signal profile with the actual signal response profile received through the detector coil 6, monitor 7 and presented to the comparator 8. In any event, the comparator 8 will generally perform a best fit analysis of the actual signal response with the stored response signals taken direct from the reference library 11 or through the compositor 12 in order to present to the memory 9 and therefore display 10 a predicted indication as to the cause of divergence and therefore unacceptability in the fluid flow 3.

The present engine monitoring arrangement and method will typically be configured whereby it is possible to deduce the particular fluid flow constituents and/or particulate content within that flow. Clearly, there is a distinction between fluid flow constituents and particulate content in that the fluid flow constituents are specifically introduced into the conduit 2 and therefore engine as a lubricant, coolant or hydraulic oil and so the operator has a choice as to the particular fluid and constituents introduced. However, with regard to particulate content it will be appreciate that such particulate content will generally be caused by wear of engine components and/or carbonation/combustion products precipitated in the fluid flow 3 as a result of engine operation. In such circumstances, deterioration in the engine and its performance should be notified through an appropriate indication indicating unacceptable operation of the engine. The display 10 through the comparator 8 and memory 9 will provide an indication of such operational divergences in the fluid flow 3 but as indicated previously will generally require authorised access in order to show underlying fluid flow constituent divergence due to the elective choices of the engine operator in terms of use of the wrong lubricant, coolant or hydraulic oil etc.

As indicated above, typically NMR interrogation deduces either specific response signals for particular component nuclei structures or a frequency shift/line broadening in the response pulse peak or a combination of both in order to identify fluid flow constituents and/or particulate content within that fluid flow 3. Normally, in accordance with the present invention the NMR interrogation procedure will enable determination of one or more of the following:— a) The underlying base carrier fluid, that is to say lubricant oil, coolant or hydraulic oil, and therefore any difference and divergence indicative of the use of the wrong underlying base carrier fluid.

b) The presence or total absence or inclusion of the required relative quantity of a specific additive to the fluid flow to achieve desired engine function and performance.

c) Determination of debris content due to engine wear or other degradation within the engine entrained within the fluid flow. This debris will typically take the form of chips or agglomerations within the fluid flow taken from specific engine components and so by appropriate analysis and deduction it is possible to identify those engine components worn, possibly the extent of such wearing and the rate of wearing for appropriate maintenance and service scheduling.

d) Determination of carbon particulates and other combustion products within the fluid flow which enables a determination of inappropriate use of a fluid in terms of it's over degradation through its operational life as a result of excessive temperatures or other conditions. Such carbonisation and combustion particulates may indicate use of the wrong fluid for a particular operation or that the engine itself for some other reason is operating at too high a temperature.

With higher degrees of sophistication particularly with regard to the reference library 11 it will be understood that not only divergence from the required fluid flow constituent types and acceptable particulate levels can be determined but also the actual type of unacceptable fluid. Thus, with regard to the base carrier fluid identification of that fluid as a lower grade lubricant, coolant or hydraulic oil may be possible. With respect to additives in addition to determining whether a particular additive is present and in the appropriate quantity it will also be possible to determine whether other additives have been included which may have a detrimental effect or have been introduced by the engine operator in order to approximate the performance of the additive which should have been incorporated. As indicated above, debris within the fluid flow may be attributable to a particular engine component or zone of the engine and so allow appropriate indication flagging to service and maintenance personnel that the engine with regard to those components or regions is excessively worn or operating beyond expected criteria to prompt them to make further investigations. Excessive carbon particulates and combustion products within the fluid flow will also indicate operation of at least parts of the engine at unacceptably high operating temperatures and again will prompt service and maintenance personnel to conduct further investigations.

Clearly, fluid flows within an engine will naturally degrade over operational cycles and service periods. In such circumstances, a similarity margin provided within the comparator 8 may also vary over an expected service interval to accommodate for such expected variations in the fluid flow 3.

The reference library 11 will generally take the form of a look-up table as indicated in which either a collection of known response signals is stored for comparison by the comparator 8 with the actual signal response received by the monitor 7 and comparator 8. The library 11 may be built progressively through appropriate calibrations of known fluid flows 3 in terms of constituent and/or debris/particulate content. The look-up table alternatively may be augmented with particular reference response signals for known constituent parts or the library 11 simply comprising those known response signals for constituents in order to provide a predictive analysis. In such circumstances, a range of known fluid flow constituents may be established within the library 11 as a base reference response signal and then through an iterative process of progressive introduction of the known signal responses for particular individual constituents possible within the flow that base reference signal response altered until a best or nearest fit comparison with the actual signal responses achieved such that a better indication as to the probable cause of divergence within the fluid flow 3 is provided.

Typically, the memory 9 will monitor the comparator 8 in order to establish a history for the actual response signal over a service period. This history may assist service and maintenance as well as designers for modification of the engine in order to improve performance.

Generally, this will form part of a larger engine health monitoring system.

Previously, as indicated, fluid in the form of lubricants, coolants and hydraulic oils have been replaced generally on a time expired basis rather than as the result of actual appreciable degradation in the fluid itself. Thus, the present invention through actual monitoring of the fluid flow 3 can determine appreciable degradation in that fluid flow and therefore signal a necessity for replacement rather than simple replacement upon a time expired basis. Similarly, in certain situations a fluid and a fluid flow may have its operational life extended by provision of additives rather than replacement of the whole fluid itself. In such circumstances, the present invention allows indication as to the necessary introduction of such additives e.g. anti-oxidants within a lubricating oil in order to maintain operational performance.

The present invention can be utilised as indicated with regard to a wide range of engines and other mechanisms in which fluids are used for lubrication, cooling, as a cutting oil or otherwise. In short, provided the fluid is presented to allow NMR interrogation and an expected response signal profile can be established then divergence from that expected response signal profile in an actual response signal can be determined in order to establish use of inappropriate fluids or constituents or presence of degradation products. Thus, the present invention can be utilised with regard to automobiles, ships, industrial turbines, static pumps, gearboxes, coolant systems, machining centres, waste release and environmental flow monitoring situations.

The present invention has the advantages of:—
a) Ensuring that correct fluids and constituents are used.
b) Providing an indication of fluid condition and chemical additive composition within a fluid flow.
c) Provides non-invasive/non-intrusive measurement of fluid flow performance and constitution.
d) Allows real time on-going fluid diagnostic appreciation of fluid flow through an engine.
e) Allows fluid flow analysis prior to destruction of analytical evidence such as through filtering etc.
f) The present engine monitoring arrangement and method can be incorporated within overall engine management arrangements.
g) The present engine monitoring arrangement and method can be utilised for control and analysis of a particular system in terms of its performance within the engine.
h) The present engine monitoring arrangement and method allows monitoring of the correct fluid flow 3 constituency for particular performance.

By allowing specific analysis and monitoring of the fluid flow 3 it will be appreciated that reservoirs of additives and replenishing fluid could be provided within the engine such that upon detection of a diminution in the particular additive or fluid a valve is actuated in order to introduce from the reservoir supplemental additives or base fluid. Similarly, through use of valve actuators it may be possible to divert degraded waste fluid from the flow. A further source of degradation within fluid flows within an engine is waxing and/or ice crystals in the oil or a fuel. In such circumstances, the present engine monitoring arrangement and method can be utilised in order to determine presence of such ice crystals or waxing and therefore activate a microwave heater to melt the crystals or wax within the oil or fuel. A particular problem with ice crystals and wax is that they tend to block filters and/or damage heat exchangers utilised within an engine. In such circumstances, by use of the present monitoring arrangement or method it will be understood that such blocking of filters or damage to heat exchangers may be eliminated.

As indicated above, typically the conduit 2 is a pipe. In such circumstances, a tuned magnetic resonance assembly is mounted around the conduit 2. The arrangement will be appropriately powered in order to create the nuclear magnetic resonance (NMR) signature of the fluid flow passing through the conduit 2. This nuclear magnetic resonance as indicated takes the form of a response signal determined by the detector ring 6 and monitor 7. The characteristic nuclear magnetic resonance signal of the fluid is compared with known expected response signals for the fluid in order to indicate a divergence in accordance with the procedure described above. As indicated, generally it is possible to provide an indication of the probable cause of divergence in terms of erroneous use of fluids and/or additives and/or debris within the fluid flow. The divergence can be linked to external actuating mechanisms which may relieve the cause of the fluid flow 3 divergence. In extreme circumstances, it may be possible for the engine to be shut down if there is sufficient degradation in the fluid flow 3 to cause serious damage to that engine. The control modules may be incorporated within a larger engine health monitoring system, the engine control, or the operator display and maintenance function.

Ideally, engine monitoring in accordance with the present arrangement and method would be in real time but generally, in view of the necessary comparison and detection delays for the nuclear magnetic response from the fluid flow analysis, will be off-set by several minutes but this will be acceptable as degradation in the fluid flow 3 will generally be gradual rather than abrupt allowing appropriate remedial action to be taken if necessary. The control modules may be incorporated within a larger engine heating numbering system, the engine control system, or the operator display and maintenance function.

As indicated above, the present engine monitoring arrangement in terms of positioning the detector ring 6 is highly flexible. Thus, the position of the detector ring 6 along with control modules may be within the engine casing or otherwise the detector 6 may be coupled to the monitor/control arrangements through cabling as required.

Although the present invention has been described with reference to a fluid flow in a conduit of a turbine engine, it will be appreciated that it may also be applied to other systems in which there is a requirement to monitor a fluid flow through a conduit.

We claim:

1. A monitoring arrangement for a fluid flow in a conduit, the arrangement comprising an NMR interrogation monitor associated with the conduit for fluid flow, the NMR interrogation monitor interrogating that fluid flow by actual response signal classification by a comparator for comparison of said fluid flow with an expected response signal and the monitor providing a specific indication as to divergence of that actual response signal from the expected response signal dependent upon the cause of that divergence.

2. An arrangement as claimed in claim 1 wherein said arrangement is a monitoring arrangement for a fluid flow in a conduit of a turbine engine.

3. An arrangement as claimed in claim 1 wherein NMR interrogation is to deduce at least one of fluid flow constituents and particulate content within that fluid flow.

4. An arrangement as claimed 1 claim wherein NMR interrogation determines at least one of specific fluid flow component nuclei, frequency shift and frequency line broadening of the actual response signal compared to the expected response signal.

5. An arrangement as claimed in claim 2 wherein the comparison between the actual response signal and the expected response signal allows determination of at last one of the following;—
   a) Difference of base carrier fluid in the fluid flow from that expected or required;
   b) One of presence and absence of relative quantity of a specific additive expected within the fluid flow;
   c) Determination of debris due to engine wear or other degradation entrained within the fluid flow;
   d) Determination of at least one of carbonisation and combustion particulates in the fluid flow;
   e) Determination of any external contaminations present in the fluid flow.

6. An arrangement as claimed in claim 5 wherein where there is difference of the base carrier fluid, the indication is to the actual carrier fluid within the fluid flow.

7. An arrangement as claimed in claim 5 wherein where determination is relative to a specific additive then the indication provides a list as to at least one of the missing additive and its quantity if different from that expected or required.

8. An arrangement as claimed in claim 5 wherein where determination is of debris due to engine wear or other degradation then the indication identifies the particular region of the engine worn or degraded and whether external debris, such as sand entering the oil system via the secondary air system and the air seals.

9. An arrangement as claimed in claim 5 wherein where the determination is of one of carbonisation and combustion particulates in the fluid flow then the indication is indicative of at least one of excess fluid flow temperature and possible identification as to the part of the engine subject to that excessive temperature.

10. An arrangement as claimed in claim 2 wherein the comparator operates by an equivalent comparison criteria between the actual signal and the expected signal determined upon acceptable similarity margins.

11. An arrangement as claimed in claim 10 wherein that similarity margin is variable dependent upon actual engine monitoring requirements.

12. An arrangement as claimed in claim 10 wherein when that equivalent comparison criteria is not met then the actual response signal is analysed for cause of divergence by comparison with a look up table of known response signals.

13. An arrangement as claimed in claim 12 wherein that look up table comprises a number of reference response signals for predictable causes of divergence and the comparison forms a best fit comparison to provide an indication as to the probable cause of divergence.

14. An arrangement as claimed in claim 12 wherein the look up table comprises known reference response signals for at least one of reference fluid constituents and additives and possible debris and combustion particulates, and a compositor projects those known response signals upon the actual signal response for a predictive cause of divergence as an indication from the comparator.

15. An arrangement as claimed in claim 14 wherein such projection is by the compositor utilising iterative comparisons from a base comparison until a nearest fit to the actual signal response is found.

16. An arrangement as claimed in claim 12 wherein a ranked list of causes of divergence is provided.

17. An arrangement as claimed in claim 1 wherein the indication of divergence provided by the comparator is only available upon authorised access.

18. A method of monitoring a fluid flow in a conduit, the method comprising monitoring the fluid flow utilising NMR interrogation to provide an actual signal, establishing an expected response signal for that NMR interrogation, comparing the actual response signal with the expected response signal and providing a specific indication as to divergence of that actual response signal from the expected response signal dependent upon the cause of that divergence.

19. A method as claimed in claim 18 wherein said method is for monitoring a fluid flow in a conduit of a turbine engine.

20. A method as claimed in claim 18 wherein NMR interrogation is to deduce fluid flow constituents and/or particulate content within that fluid flow.

21. A method as claimed in claim 18 wherein NMR interrogation determines at least one of specific fluid flow component nuclei, frequency shift and frequency line broadening of the actual response signal compared to the expected response signal.

22. A method a s claimed in claim 19 wherein the comparison between the actual response signal and the expected response signal allows determination of one or more of the following;—
   a) Difference of base carrier fluid in the fluid flow from that expected or required;
   b) Presence or absence of relative quantity of a specific additive expected within the fluid flow;
   c) Determination of debris due to engine wear or other degradation entrained within the fluid flow;
   d) Determination of carbonisation and/or combustion particulates in the fluid flow;
   e) Determination of external contaminants in the fluid flow.

23. A method as claimed in claim 19 wherein the comparison is by an equivalent comparison criteria between the actual signal and the expected signal determined upon acceptable similarity margins.

24. A method as claimed in claim 23 wherein that similarity margin is variable dependent upon actual monitoring requirements.

25. A method as claimed in claim 18 wherein when that equivalent comparison criteria is not met then the actual response signal is analysed for cause of divergence by comparison with a look up table of known response signals.

26. A method as claimed in claim 18 wherein a ranked list of causes of divergence is provided.

* * * * *